(12) United States Patent
Lee

(10) Patent No.: US 8,472,779 B2
(45) Date of Patent: Jun. 25, 2013

(54) CONCURRENTLY DISPLAYING MULTIPLE TRICK STREAMS FOR VIDEO

(75) Inventor: Victor S. Lee, Cupertino, CA (US)

(73) Assignee: Microsoft Corporation, Redmond, WA (US)

( * ) Notice: Subject to any disclaimer, the term of this patent is extended or adjusted under 35 U.S.C. 154(b) by 840 days.

(21) Appl. No.: 12/141,064

(22) Filed: Jun. 17, 2008

(65) Prior Publication Data
US 2009/0310933 A1 Dec. 17, 2009

(51) Int. Cl.
*H04N 5/91* (2006.01)

(52) U.S. Cl.
USPC .............................. 386/68; 386/343; 386/353

(58) Field of Classification Search
USPC .......................................................... 386/68
See application file for complete search history.

(56) References Cited

U.S. PATENT DOCUMENTS

| | | | |
|---|---|---|---|
| 5,576,902 | A | 11/1996 | Lane et al. |
| 6,396,999 | B1 | 5/2002 | Van Gestel |
| 7,177,522 | B2 | 2/2007 | MacInnis |
| 7,260,307 | B2 * | 8/2007 | Lin et al. ........................ 386/230 |
| 7,274,857 | B2 | 9/2007 | Nallur et al. |
| 2003/0002854 | A1 | 1/2003 | Belknap et al. |
| 2004/0128317 | A1 * | 7/2004 | Sull et al. .................... 707/104.1 |
| 2004/0151471 | A1 * | 8/2004 | Ogikubo .......................... 386/52 |
| 2005/0212968 | A1 | 9/2005 | Ryal |
| 2006/0104609 | A1 * | 5/2006 | Ohmori et al. ................... 386/68 |
| 2007/0002045 | A1 | 1/2007 | Finger et al. |
| 2007/0019925 | A1 | 1/2007 | MacInnis |
| 2007/0189717 | A1 | 8/2007 | Yun et al. |
| 2008/0043140 | A1 | 2/2008 | Herpel et al. |
| 2008/0155585 | A1 * | 6/2008 | Craner et al. .................... 725/32 |
| 2009/0172543 | A1 * | 7/2009 | Cronin et al. .................. 715/721 |

OTHER PUBLICATIONS

Li et al. "Browsing Digital Video", Proceedings of the SIGCHI conference on Human Factors in computing systems, ACM 2000, 8 Pages.*
"CineView HD LE", 2005, Vela LP., pp. 2.
"DVR-810: High Definition Digital Video Recorder", retrieved at <<http://www.digitalview.com.au/DVR810_Brochure_OL.pdf>>, Digitalview, pp. 4.

* cited by examiner

*Primary Examiner* — Jeffrey Pwu
*Assistant Examiner* — Helai Salehi
(74) *Attorney, Agent, or Firm* — Wolfe-SBMC

(57) ABSTRACT

In accordance with one or more aspects, multiple trick streams corresponding to video content are concurrently displayed in multiple windows. A user selection of one window of the multiple windows is received, and the video content is played back at a location corresponding to a location in a trick stream being played back in the one window when the user selection is received.

20 Claims, 6 Drawing Sheets

CONCURRENTLY DISPLAYING MULTIPLE TRICK STREAMS FOR VIDEO

BACKGROUND

Current video playback systems typically allow consumers to rewind or fast-forward through the video, oftentimes allowing a user to select one of a few different speeds at which the fast-forwarding or rewinding can be performed. Some systems also allow slow-motion playback of video, oftentimes allowing a user to select one of a few different speeds at which the slow-motion playback can be performed. However, such techniques can make it difficult for users to find a particular location in the video because if they go too quickly they may miss the location they are looking for, whereas if they go too slowly it may take a long time to find the location they are looking for. These current rewind, fast-forward, and slow-motion techniques can thus be problematic and can create frustrating user experiences.

SUMMARY

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

In accordance with one or more aspects of the concurrently displaying multiple trick streams for video, a request to display multiple different trick streams corresponding to video content is received. In response to the request, multiple different windows are concurrently displayed, and a different one of the multiple different trick streams is displayed in each of the multiple different windows. A request to stop display of the multiple different trick streams is received, and a user selection of one of the multiple different windows is received. The video content is then played back at a location corresponding to a current location of the trick stream in the selected window.

In accordance with one or more aspects of the concurrently displaying multiple trick streams for video, multiple trick streams corresponding to video content are concurrently displayed in multiple windows. A user selection of one window of the multiple windows is received, and the video content is played back at a location corresponding to a location in a trick stream being played back in the one window when the user selection is received.

In accordance with one or more aspects of the concurrently displaying multiple trick streams for video, a device comprises a video content display module to receive and display video content, and a trick stream display module. The trick stream display module is to concurrently display, in each of multiple windows, one of multiple trick streams corresponding to the video content, and further to communicate to the video content display module a location of the video content corresponding to a user selection of one of the multiple different windows. The video content display module is further to jump to displaying the video content at the location communicated by the trick stream display module.

BRIEF DESCRIPTION OF THE DRAWINGS

The same numbers are used throughout the drawings to reference like features.

DETAILED DESCRIPTION

Concurrently displaying multiple trick streams for video is discussed herein. Multiple windows corresponding to video content are displayed, and within each of these windows a different trick stream corresponding to the video content is displayed. These different trick streams can include, for example, fast-forward streams, rewind streams, and/or slow-motion streams of various speeds. A user can then select one of these windows and have the display of the video content jump to a location corresponding to the location of the trick stream being displayed in the selected window.

Figure 1:
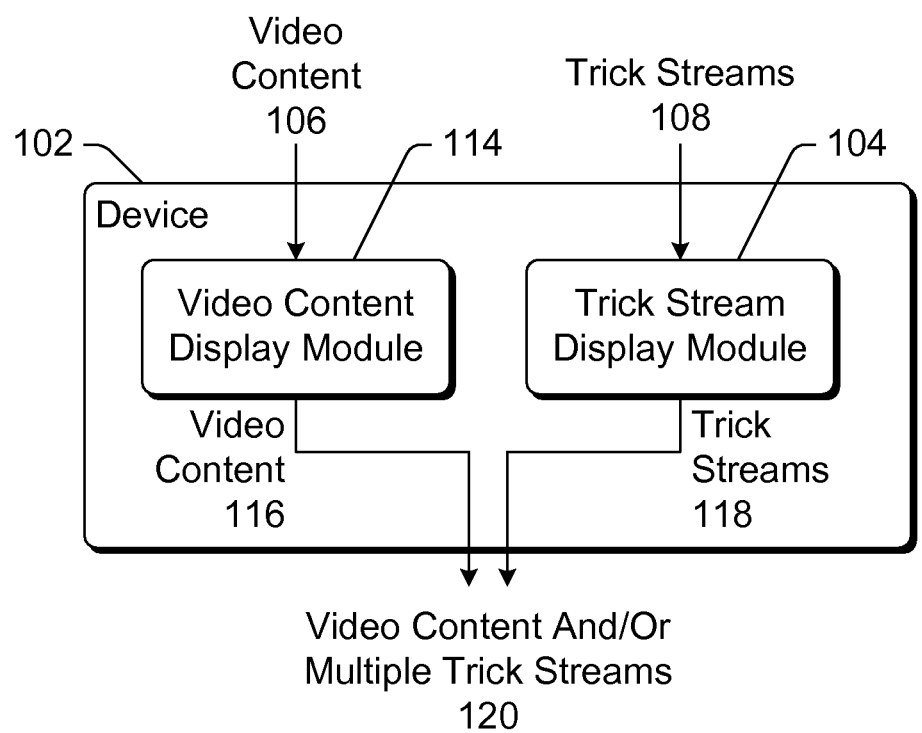
FIG. 1 illustrates an example system implementing the concurrently displaying multiple trick streams for video in accordance with one or more embodiments.

FIG. 1 illustrates an example system 100 implementing the concurrently displaying multiple trick streams for video in accordance with one or more embodiments. System 100 includes a device 102 including a trick stream display module 104 and a video content display module 114. Device 102 can be any of a variety of devices that generate video for display. For example, device 102 can be a computer, such as a desktop computer, a mobile station, an entertainment appliance, a set-top box communicatively coupled to a display device, video playback devices (e.g., digital video recorder (DVR), digital versatile disk (DVD) player, etc.), a cellular or other wireless phone, a game console, an automotive PC, and so forth. Thus, device 102 can range from full resource devices with substantial memory and processor resources (e.g., personal computers, game consoles, etc.) to a low-resource device with limited memory and/or processing resources (e.g., traditional set-top boxes, hand-held game consoles, DVD players, etc.). Although modules 104 and 114 are illustrated as being part of the same device, alternatively modules 104 and 114 can be implemented by different devices. Additionally, although modules 104 and 114 are illustrated as being separate modules, alternatively modules 104 and 114 can be implemented as a single module.

Video content display module 114 receives video content 106, converts video content 106 as appropriate into a format that can be displayed by a display device, and outputs the converted video content as video content 116. Accordingly, video content display module 114 displays or plays back video content 106. Video content display module 114 also optionally extracts particular content from video content 106, such as by tuning to a particular channel, by selecting a particular stream, and so forth. Other types of content corresponding to video content 106, such as audio content, are also oftentimes received by device 102. Video content 106 can include a variety of different types of programs. For example, video content 106 can include movies, sitcoms, commercials, news broadcasts, documentaries, sporting events, and so forth.

Trick stream display module 104 accesses multiple trick streams 108 corresponding to video content 106 (and thus also corresponding to video content 116). Trick stream display module 104 can receive one or more trick streams 108 from a source, being the same source or a different source from which video content 106 is received. Alternatively, trick streams 108 can be generated by device 102 (e.g., by module 104 or alternatively another component or module of device 102). For example, a module of device 102 (e.g., module 104 or alternatively another module) can access video content 106 and generate one or more of trick streams 108.

Trick streams 108 can be pre-generated based on video content 106 and stored (e.g., at the same location as video content 106 is stored or elsewhere). For example, a remote source may store both video content 106 and trick streams 108, both video content 106 and trick streams 108 may be stored on a DVD or other local source, and so forth. Accordingly, when one or more of trick streams 108 are to be displayed, these stored trick streams are retrieved and displayed. Alternatively, trick streams 108 can be generated on-the-fly based on video content 106. Accordingly, when one or more of trick streams 108 are to be displayed, these trick streams are generated.

Video content 106 and trick streams 108 can be received from a variety of different sources. These sources can be local sources, such as a hard disk or DVD that is inserted into, coupled to, or included as part of device 102. These sources can also be remote sources, such as one or more remote servers, one or more broadcast centers or other content distributors, or other devices making content 106 and/or trick streams 108 available to device 102. Remote sources can make content 106 and/or trick streams 108 available via any of a variety of transmission media, such as one or more of the Internet, a wide area network (WAN), a local area network (LAN), a wireless network, a telephone network, an intranet, a terrestrial analog or digital signal, a cable system, a satellite system, and so forth.

In one or more embodiments, device 102 displays video content and/or multiple trick streams 120. Accordingly, device 102 can be or can include, for example, a television, a monitor, an LCD, a projector, or some other television-based display system. In other embodiments device 102 generates a video signal based on video content and/or multiple trick streams 120 that is output to one or more other devices which in turn display video content and/or multiple trick streams 120. This video signal can be output using a variety of different communication links, such as an RF (radio frequency) link, an S-video link, a composite video link, a component video link, a DVI (digital video interface), and so forth. Device 102 also typically plays back other content associated with video content and/or multiple trick streams 120, such as audio content and/or metadata content (e.g., closed captioning or other data), or generates a signal based on this other content that is output to one or more other devices to play back or otherwise present the content.

Trick streams 108 correspond to video content 106 and refer to versions of video content 106 to be displayed in a different playback direction and/or speed than video content 106. Trick streams 108 can include different types of streams, such as rewind streams (which are versions of video content 106 in a different playback direction than video content 106) having various speeds, fast-forward streams having various speeds, slow-motion streams having various speeds, and so forth. The speeds of trick streams refer to how fast the video in the tricks streams is displayed. For example, the standard display speed of video content 106 can be referred to as 1×. This refers to the display of the video content 106 as it is normally played back to users. A particular fast-forward that is played back with a display of video twice that of video content 106 would then be referred to as a 2× stream. Similarly, a slow-motion stream that is played back with a display of video half that of video content 106 would then be referred to as a 0.5× stream. Rewind streams can also have different speeds, such as 0.5×, 2×, 8×, and so forth. It is to be appreciated that these speeds are only examples, and that a variety of different speeds can be used, including speeds faster than 8× and speeds slower than 0.5×.

Trick streams 108 can be generated in a variety of different manners using techniques that are well-known to those skilled in the art. For example, particular frames of video content 106 can be selected according to some criteria (e.g., every other frame, every fifth frame, etc.), a content author or distributor can flag particular frames of video content 106 to be included in different trick streams, frames of video can be displayed at a slower rate (e.g., 15 frames per second rather than a standard 30 frames per second) or at a faster rate (e.g. 45 frames per second rather than a standard 30 frames per second), and so forth.

Trick stream display module 104 displays multiple different windows concurrently, displaying a different trick stream 118 in each of these different windows. These trick streams 118 are selected and/or generated ones of trick streams 108. Accordingly, these trick streams 118 are associated with video content 106 and video content 116. One or both of video content 116 and trick streams 118 are displayed by device 102. Alternatively, a video signal based on one or both of video content 116 and trick streams 118 is output to one or more other devices which in turn display one or both of trick streams 118 and video content 116.

Multiple ones of trick streams 118 are displayed concurrently. These can be the same type of trick stream (e.g., multiple fast-forward streams, multiple rewind streams, multiple slow-motion streams), or alternatively different types of trick streams (e.g., one or more fast-forward streams and one or more rewind streams).

Figure 2:
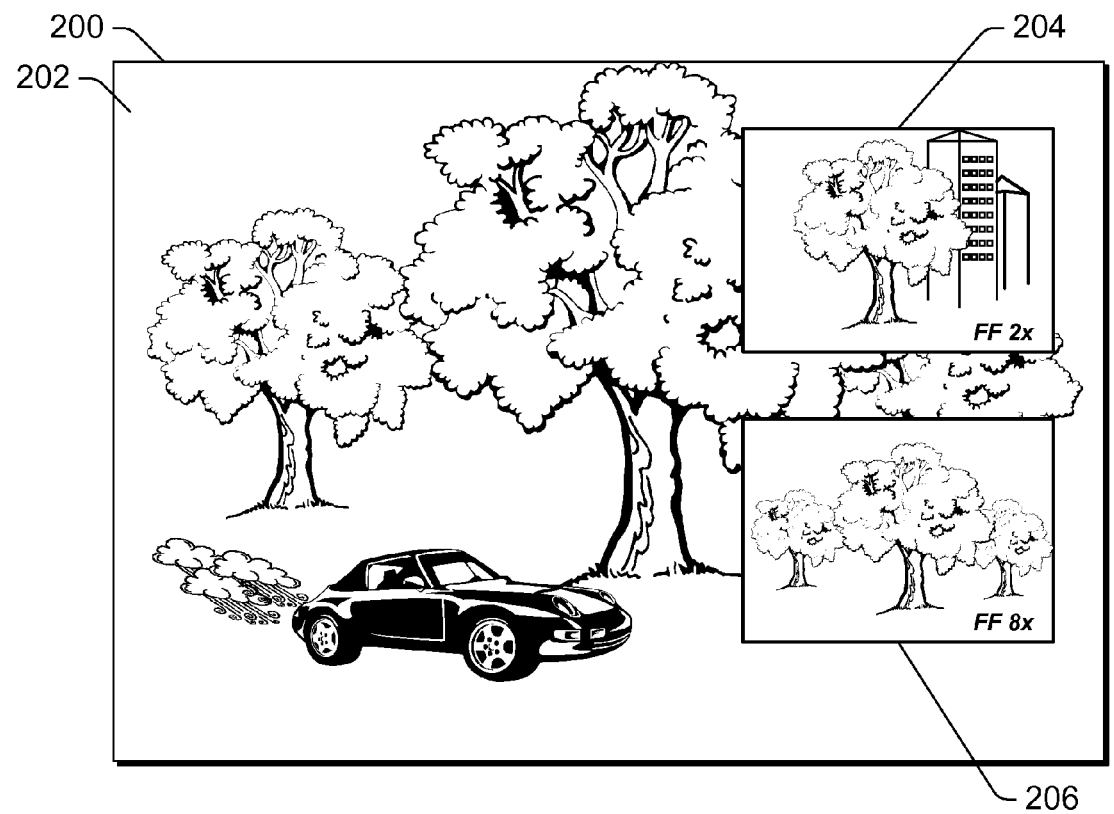
FIG. 2 illustrates an example of concurrently displaying multiple trick streams for video in accordance with one or more embodiments.

FIG. 2 illustrates an example of concurrently displaying multiple trick streams for video in accordance with one or more embodiments. A display 200 includes a full-screen or full-window portion 202 in which video content is displayed. This video content is, for example, video content 116 of FIG. 1 as output by module 114. Display 200 also includes two windows 204 and 206, each displaying a different trick stream corresponding to the video content displayed in portion 202. These trick streams are, for example, trick streams 118 of FIG. 1. Although only two windows 204 and 206 are illustrated in display 200, it is to be appreciated that one or more additional windows can also be included in display 200.

Window 204 displays a trick stream that is a 2× fast-forward stream, an indicator of which ("FF 2×") is displayed in window 204. Window 206 displays a trick stream that is an 8× fast-forward stream, an indicator of which ("FF 8×") is displayed in window 206. As can be seen in FIG. 2, two different trick streams (a 2× fast-forward stream and an 8× fast-forward stream) are displayed concurrently in display 200. Additionally, it should be noted that the trick stream indicators ("FF 2×" and "FF 8×") are optional and alternatively are not displayed in window 204 and/or 206.

Figure 3:
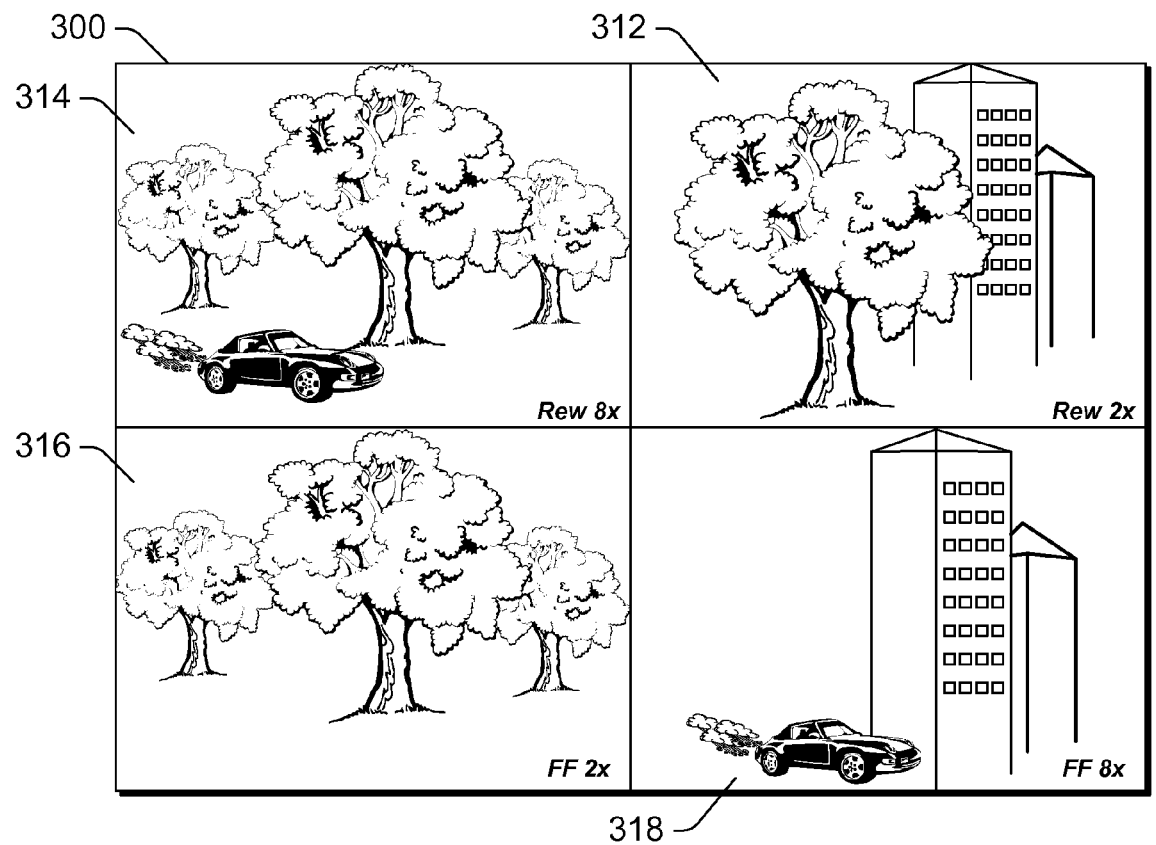
FIG. 3 illustrates another example of concurrently displaying multiple trick streams for video in accordance with one or more embodiments.

FIG. 3 illustrates another example of concurrently displaying multiple trick streams for video in accordance with one or more embodiments. A display 300 is separated into four different portions 312, 314, 316, and 318. Each portion 312, 314, 316, and 318 is a different window within which a different trick stream is displayed. Each of the different trick streams corresponds to, for example, video content 116 of FIG. 1. These trick streams are, for example, trick streams 118 of FIG. 1. Although four windows 312, 314, 316, and 318 are illustrated in display 300, it is to be appreciated that one or more additional windows can also be included in display 300, or that fewer than four windows can be included in display 300.

Window 312 displays a trick stream that is a 2× rewind stream, an indicator of which ("Rew 2×") is displayed in window 312. Window 314 displays a trick stream that is an 8× rewind stream, an indicator of which ("Rew 8×") is displayed in window 314. Window 316 displays a trick stream that is a 2× fast-forward stream, an indicator of which ("FF 2×") is displayed in window 316. Window 318 displays a trick stream that is an 8× fast-forward stream, an indicator of which ("FF 8×") is displayed in window 318. As can be seen in FIG. 3, four different trick streams (a 2× rewind stream, an 8× rewind stream, a 2× fast-forward stream, and an 8× fast-forward stream) are displayed concurrently in display 300. Additionally, it should be noted that the trick stream indicators ("Rew 2×", "Rew 8×", "FF 2×", and "FF 8×") are optional and alternatively are not displayed in one or more of windows 312-316.

Figure 4:
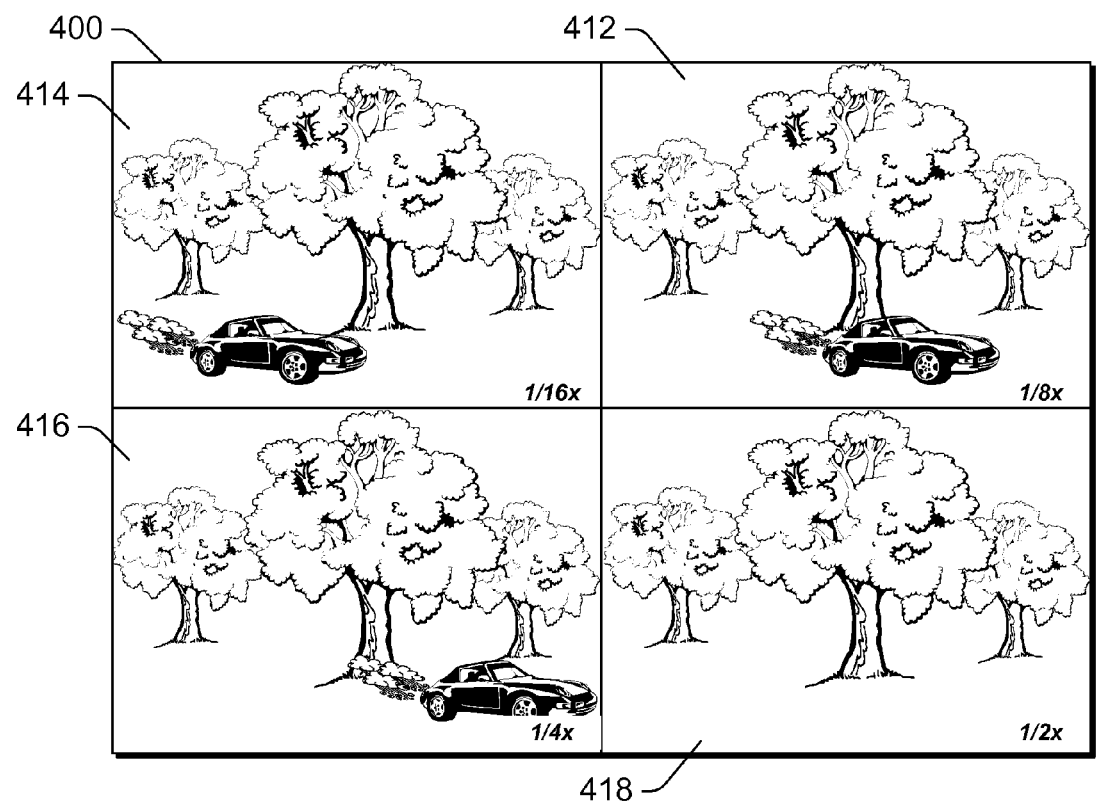
FIG. 4 illustrates another example of concurrently displaying multiple trick streams for video in accordance with one or more embodiments.

FIG. 4 illustrates another example of concurrently displaying multiple trick streams for video in accordance with one or more embodiments. A display 400 is separated into four different portions 412, 414, 416, and 418. Each portion 412, 414, 416, and 418 is a different window within which a different trick stream is displayed. Each of the different trick streams corresponds to, for example, video content 116 of FIG. 1. These trick streams are, for example, trick streams 118 of FIG. 1. Although four windows 412, 414, 416, and 418 are illustrated in display 400, it is to be appreciated that one or more additional windows can also be included in display 400, or that fewer than four windows can be included in display 400.

Window 414 displays a trick stream that is a ¹⁄₁₆× slow-motion stream, an indicator of which ("¹⁄₁₆×") is displayed in window 414. Window 412 displays a trick stream that is a ⅛× slow-motion stream, an indicator of which ("⅛×") is displayed in window 412. Window 416 displays a trick stream that is a ¼× slow-motion stream, an indicator of which ("¼×") is displayed in window 416. Window 418 displays a trick stream that is a ½× slow-motion stream, an indicator of which ("½×") is displayed in window 418. As can be seen in FIG. 4, four different slow-motion trick streams are displayed concurrently in display 400. Additionally, it should be noted that the trick stream indicators ("¹⁄₁₆×", "⅛×", "¼×", and "½×") are optional and alternatively are not displayed in one or more of windows 412-416.

With respect to FIGS. 2, 3, and 4, it is to be appreciated that the display of windows in displays 200, 300, and 400 are only examples. Windows can be displayed in any of a variety of different manners. For example, windows can be different sizes and or shapes than illustrated in FIGS. 2, 3, and 4, can be situated in different locations than illustrated in FIGS. 2, 3, and 4, and so forth.

Returning to FIG. 1, multiple different windows are opened or generated, within which different trick streams 118 are displayed. These different windows can be opened or generated by trick stream display module 104, or alternatively another component or module of device 102. Windows can be opened or generated in a variety of different manners, such as creation of a new window by a computer operating system (e.g., one or more of the Microsoft® Windows® operating systems), a picture-in-picture (PIP) window on a television display device, and so forth. Windows in which trick streams 118 are displayed can be displayed in different manners, such as windows overlaying video as shown in FIG. 2, as separate portions of the display as shown in FIGS. 3 and 4, and so forth. Additionally, if multiple displays are available (e.g., multiple LCDs, multiple projectors, etc.), then different windows can be opened on different ones of these displays. Which particular trick stream 118 is displayed in which particular window can be determined in different manners, such as according to some predetermined setting, randomly, in accordance with some other rules or criteria, and so forth.

The different trick streams 118 and video content 116 are output by device 102 as video content and/or multiple trick streams 120. In one or more embodiments, trick streams 118 are displayed concurrently with video content 116. This concurrent display of trick streams 118 with video content 116 can be accomplished in different manners, such as displaying multiple windows overlaying video content 116 as illustrated in FIG. 2. Alternatively, this concurrent display of trick streams 118 with video content 116 can be accomplished in other manners, such as displaying video content 116 in one window and the trick streams 118 in other windows, re-sizing the portion of the display in which video content 116 is displayed to leave a portion (e.g., a bar along one side or the top or bottom of the display) in which the windows can be displayed, and so forth. In one or more embodiments, playback of video content 116 continues while the trick streams 118 are displayed in the windows. Alternatively, playback of video content 116 can be paused while the trick streams 118 are displayed in the windows.

Alternatively, trick streams 118 are displayed separately from video content 116, in which case one but not both of content 116 and trick streams 118 are displayed at a time. This separate display of trick streams and video content 116 can be accomplished in different manners, such as dividing the display into multiple portions and having each portion be a window in which a trick stream is displayed as illustrated in FIGS. 3 and 4. Alternatively, this separate display of trick streams 118 and video content 116 can be accomplished in other manners, such as displaying windows as illustrated in FIG. 2 but not displaying the video content (e.g., leaving portion 202 of FIG. 2 blank).

The concurrent display of multiple trick streams can be initiated in a variety of different manners. In one or more embodiments, the concurrent display of multiple trick streams is initiated in response to a user request. For example, the user can press or otherwise activate a button on a remote control device, a button on device 102, a menu or other on-screen option displayed by device 102, and so forth. A dedicated "multiple trick streams" button or option can be made available, or alternatively other buttons or options can be configured to initiate the concurrent display of multiple trick streams. For example, a "fast-forward" button on a remote control device can be configured (e.g., optionally via a user-selectable setting) to initiate the concurrent display of multiple fast-forward trick streams whenever the button is activated.

Additionally, different buttons or options can be associated with different types of trick streams. For example, one button or option can be associated with fast-forward streams so that multiple fast-forward streams are concurrently displayed when that button or option is activated. Similarly, another button or option can be associated with rewind streams, another button or option can be associated with slow-motion streams, and so forth. Alternatively, a single button or option can be used for multiple types of trick streams and, after the button or option is activated, another option displayed allowing the user to select one or more types of trick streams and/or one or more speeds of the trick streams. For example, after the button or option is activated, a user interface can be displayed or otherwise presented to the user allowing the user to select one or more types of trick streams and/or one or more speeds of the trick streams. One or more default settings can be made available for the user to select (e.g., fast-forward streams at 2×, 8×, and 16× speeds; rewind streams at 3×, 6×, and 9× speeds; and so forth).

The number of windows concurrently displaying trick streams can be identified in different manners. In one or more embodiments, device 102 exposes a user-selectable setting allowing the user to select a number of windows that he or she desires, as well as what trick streams (e.g., direction and/or speed) that he or she desires to have displayed in those windows. When the multiple trick streams are concurrently displayed, this user-selected number of windows is opened with the user-selected trick streams being displayed therein. These user selections can be saved as a configuration parameter of device 102, or alternatively can be input by the user when initiating concurrent display of multiple trick streams (e.g., after activating a button or other option to concurrently display multiple trick streams).

Alternatively, rather than being initiated in response to a user request, the concurrent display of multiple trick streams can be initiated in response to other requests. Such other requests can be, for example, received from another component or module of device 102, received from a component or module of another device, embedded in video content 106, and so forth.

Playback of each of the trick streams begins at a particular location of video content 106. This particular location can be a fixed location (e.g., the beginning of a particular program included in video content 106, the ending of a particular program included in video content 106, at approximately a midpoint of a particular program included in video content 106, and so forth). Alternatively, this location can be a variable location (e.g., the location of video content 106 being displayed when the concurrent display of the multiple trick streams is initiated, a location specified by the user, and so forth).

Additionally, it should be noted that the particular locations for different windows can be different. For example, playback of the trick stream in a rewind window may begin at one location (e.g., at the ending of a particular program included in video content 106), while playback of the trick stream in a fast-forward window may being at a different location (e.g., at the beginning of the particular program included in video content 106).

The location where the playback of the trick streams begins can be determined in a variety of different manners. In one or more embodiments, different buttons (e.g., on device 102, on a remote control device associated with device 102, displayed by device 102, and so forth) can correspond to different locations. For example, one button may correspond to the beginning of a particular program included in video content 106, another button may correspond to the ending of a particular program included in video content 106, and so forth. Alternatively, other techniques can be used, such as the user identifying the locations for the trick streams in the different windows when the concurrent display of the multiple trick streams is initiated, the user having set one or more configuration values or parameters of device 102 to identify the locations for the trick streams in the different windows, retrieving an indication of the locations for the trick streams in the different windows from video content 106 (or metadata corresponding to video content 106), and so forth.

As the multiple trick streams are being concurrently displayed in different windows, each window typically displays a different location of video content 106 at any particular time. For example, at a particular time one window may be displaying a location of video content 106 that is 3 minutes and 20 seconds into video content 106 (e.g., 3 minutes and 20 seconds after the start of a program), while another window is displaying a location of video content 106 that is 23 minutes and 15 seconds into video content 106 (e.g., 23 minutes and 15 seconds after the start of the program).

Location identification information can also optionally be displayed to identify to the user the location in video content 106 being displayed in a window. For example, a progress bar can be associated with each window, the beginning of the progress bar corresponding to the beginning of the particular program included in video content 106, and the ending of the progress bar corresponding to the ending of the particular program included in video content 106. An arrow, line, bar, or other identifier can then be used to identify on the progress bar the location of the particular program included in video content 106 being displayed in that window at any given time.

While the multiple trick streams are being concurrently displayed in different windows, a user of device 102 can select one of the windows. Although discussed herein primarily as user selection of a window, it is to be appreciated that this user selection is also a selection of the particular trick stream being displayed in that window.

In response to this user selection of a window, trick stream display module 104 closes the multiple windows displaying the multiple trick streams. Trick stream display module 104 communicates the location of video content 106 that the selected window is playing back at the time this selection is received. Video content display module 114 then begins displaying video content 106 at the location identified by module 104. This is also referred to as display or playback of video content 106 jumping to the location identified by module 104.

By way of example, referring back to FIG. 2, assume that a user selects window 206 being shown on display 200. In response to this selection, windows 204 and 206 are both closed, and playback of the video content in full-screen or full-window portion 202 jumps to the location of the video corresponding to the trick stream being displayed in window 206. Accordingly, full-screen or full-window portion 202 begins displaying the video content at the location that was being displayed in window 206 when selected by the user.

Returning to FIG. 1, a user can make a selection of one of the multiple trick streams being concurrently displayed in a variety of different manners. In one or more embodiments, a particular window is highlighted or otherwise distinguished from the other windows being displayed. The user can change which window is highlighted, effectively moving the highlighting, in a variety of different manners, such as using inputs on a remote control device associated with device 102 (e.g., directional or arrow buttons, a scroll button or pad, and so forth), using inputs on device 102 (e.g., directional or arrow buttons, a scroll button or pad, and so forth), by inputting voice commands, by selecting an on-display button (e.g., using a pointer displayed by device 102 and a cursor control device), and so forth. The highlighted or otherwise distinguished window is then selected by the user inputting a "play" or "jump to" command. This "play" or "jump to" command can be input in different manners, such as activation of a particular button on a remote control device associated with device 102, activation of a button on the device 102, activation of a button on device 102, input of a verbal command, selection of an on-display button (e.g., using a pointer displayed by device 102 and a cursor control device), and so forth.

In other embodiments, a user can make a selection of one of the multiple trick streams being concurrently displayed in different manners. For example, each window being displayed may have a corresponding identifier (e.g., 1, 2, 3, 4, etc.) that can optionally be displayed in the window. A particular one of those windows can be selected by a user activating a button (e.g., on device 102 and/or on a remote control device associated with device 102) corresponding to the identifier (e.g., a "1" button, a "2" button, etc.). By way of another example, a particular window can be highlighted or otherwise distinguished as the "selection" window, and the user can change which of the multiple trick streams being concurrently displayed is displayed in that selection window at any given time. The user can change which window is displayed in the selection window in different manners, analogous to the discussion above regarding changing which window is highlighted. The selection window is then selected by the user inputting a "play" or "jump to" command, analogous to the discussion above regarding changing which window is highlighted.

Additionally, in one or more embodiments a set of one or more rules can be used to pause or stop playback in a particular window based on particular criteria. This criteria can take a variety of different forms, such as reaching a particular location in the video (e.g., the end of a program, the beginning of a program, a midpoint of a program, etc.), after a particular percentage of the video has already been displayed in the window (e.g., 30% or 50% of a program has already been displayed in fast-forward, rewind, or slow-motion in the window), after a particular amount of time has elapsed (e.g., video has been displayed in fast-forward, rewind, or slow-motion in the window for 30 seconds, 2 minutes, etc.), and so forth.

Figure 5:
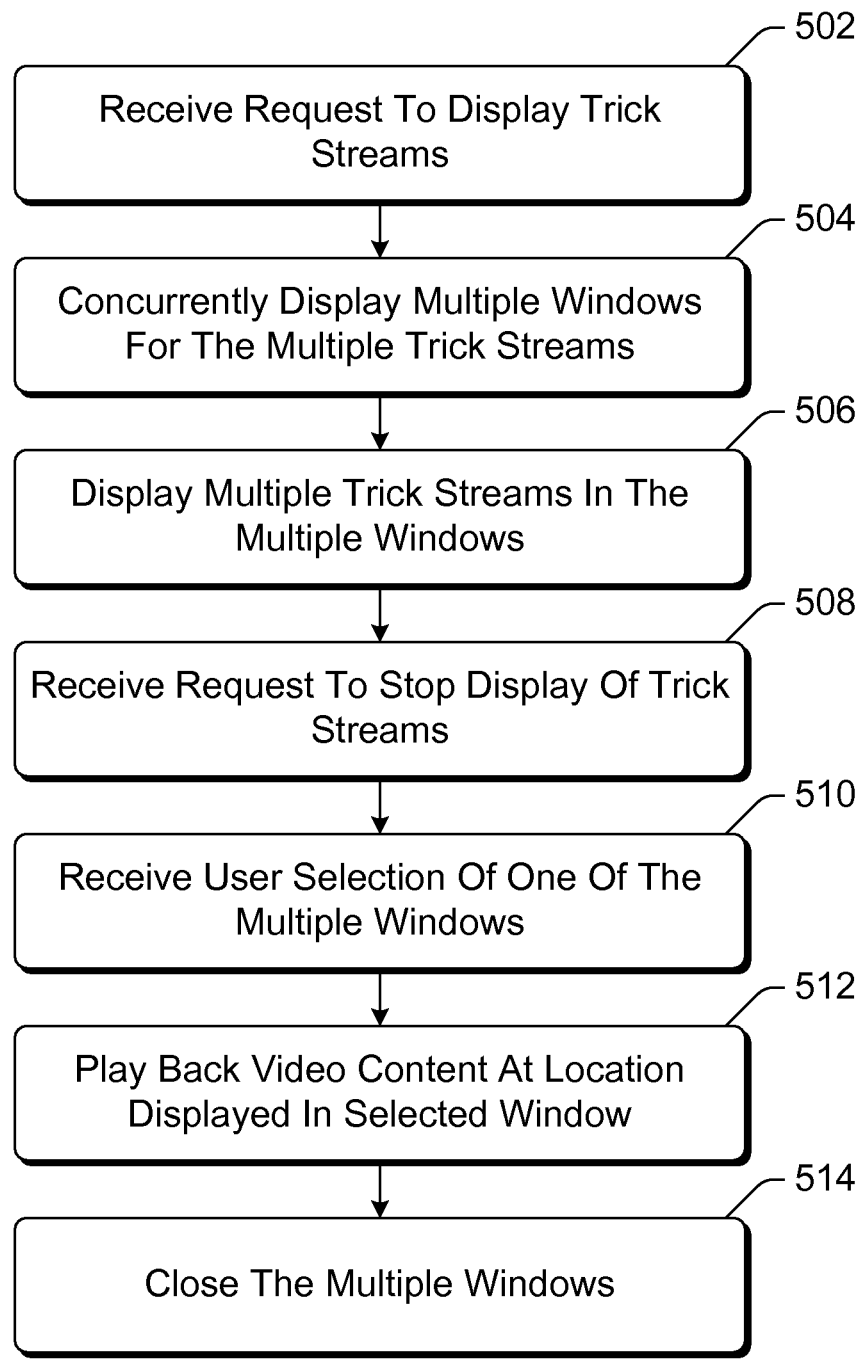
FIG. 5 is a flowchart illustrating an example process for concurrently displaying multiple trick streams for video in accordance with one or more embodiments.

FIG. 5 is a flowchart illustrating an example process 500 for concurrently displaying multiple trick streams for video in accordance with one or more embodiments. Process 500 can be implemented in software, firmware, hardware, or combinations thereof Process 500 can be carried out, for example, by a device such as device 102 of FIG. 1. Process 500 is an example process for implementing concurrently displaying multiple trick streams for video; additional discussions of concurrently displaying multiple trick streams for video are included herein with reference to different figures.

In process 500, a request to display the trick streams is received (act 502). As discussed above, this request can be received in a variety of different manners from a variety of different sources. In response to the request, multiple windows for the multiple trick streams are concurrently displayed (act 504). As discussed above, the number of windows displayed in act 504 can be determined in a variety of different manners.

Additionally, multiple trick streams are displayed in these multiple windows (act 506). Each window displays a different one of the multiple trick streams. As discussed above, the particular trick stream displayed in each window, as well as the location of the video content where display of each stream begins, can be determined in a variety of different manners.

A request to stop the display of the multiple trick streams is received (act 508). This request can be an explicit request, such as user selection of a "pause" or "stop" button. Alternatively, this request can be an implicit request, such as user selection of a particular one of the windows displayed in act 504 (in which case acts 508 and 510 are combined in a single act). Displays of a trick stream in a window can also be stopped in response to other rules, as discussed above.

A user selection of one of the windows displayed in act 504 is also received (act 510). This user selection of a window can be received in a variety of different manners as discussed above.

Playback of the video content jumps to the location being displayed in the trick stream of the selected window (act 512). This is the current location of the trick stream being displayed in the selected window at the time the user selected the window. Additionally, the windows displayed in act 504 are closed (act 514).

Additionally, it should be noted that, although the trick streams are discussed herein primarily as playing back video content, one or more other types of content can also be displayed or otherwise presented in addition to, or in place of, the video content. By way of example, metadata corresponding to the video content (e.g., closed captioning or other data) can be displayed with the video of the trick stream. By way of another example, this metadata can be displayed as a trick stream without displaying the video of the trick stream. By way of yet another example, audio content corresponding to the video content can be played back along with the video content of the trick stream.

Figure 6:
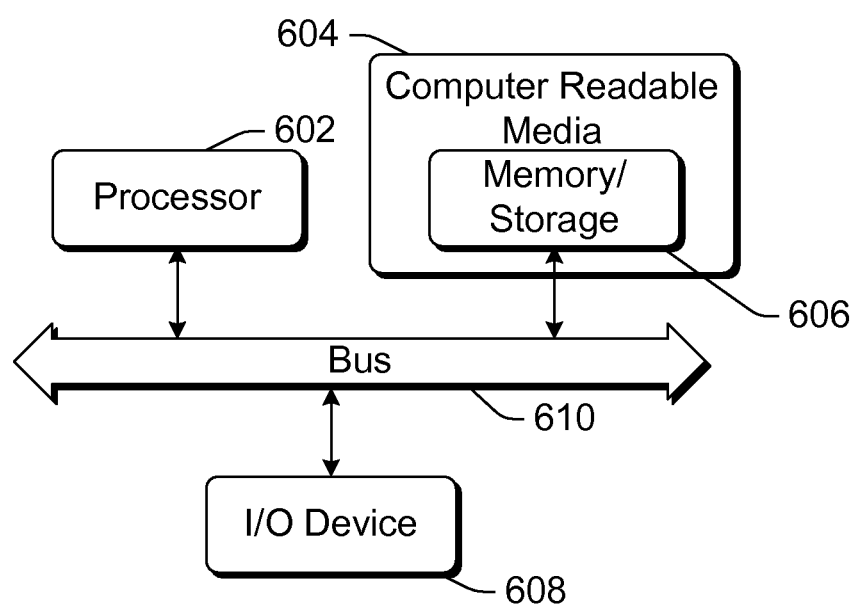
FIG. 6 illustrates an example computing device that can be configured to implement the concurrently displaying multiple trick streams for video in accordance with one or more embodiments.

FIG. 6 illustrates an example computing device 600 that can be configured to implement the concurrently displaying multiple trick streams for video in accordance with one or more embodiments. Computing device 600 can be, for example, device 102 of FIG. 1. Computing device 600 can implement any of the techniques and processes discussed herein. Alternatively, the techniques and processes discussed herein can be distributed across multiple computing devices 600.

Computing device 600 includes one or more processors or processing units 602, one or more computer readable media 604 which can include one or more memory and/or storage components 606, one or more input/output (I/O) devices 608, and a bus 610 that allows the various components and devices to communicate with one another. Computer readable media 604 and/or I/O device(s) 608 can be included as part of, or alternatively may be coupled to, computing device 600. Bus 610 represents one or more of any of several types of bus structures, including a memory bus or memory controller, a peripheral bus, an accelerated graphics port, and a processor or local bus using any of a variety of bus architectures. Bus 610 can include wired and/or wireless buses.

Memory/storage component 606 represents one or more computer storage media. Component 606 can include volatile media (such as random access memory (RAM)) and/or non-volatile media (such as read only memory (ROM), Flash memory, optical disks, magnetic disks, and so forth). Component 606 can include fixed media (e.g., RAM, ROM, a fixed hard drive, etc.) as well as removable media (e.g., a Flash memory drive, a removable hard drive, an optical disk, and so forth).

The techniques and processes discussed herein can be implemented in software, with instructions being executed by processing unit 602. It is to be appreciated that different instructions can be stored in different components of computing device 600, such as in processing unit 602, in various cache memories of processing unit 602, in other cache memories of device 600 (not shown), on other computer readable media, and so forth. Additionally, it is to be appreciated that the location where instructions are stored in computing device 600 can change over time.

One or more input/output devices 608 allow a user to enter commands and information to computing device 600, and also allow information to be presented to the user and/or other components or devices. Examples of input devices include a remote control device, a keyboard, a cursor control device (e.g., a mouse), a microphone, a scanner, and so forth. Examples of output devices include a display device (e.g., a monitor or projector), speakers, a printer, a network card, and so forth.

Various techniques and processes may be described herein in the general context of software or program modules. Generally, software includes routines, programs, objects, components, data structures, and so forth that perform particular tasks or implement particular abstract data types. An implementation of these modules and techniques may be stored on or transmitted across some form of computer readable media. Computer readable media can be any available medium or media that can be accessed by a computing device. By way of example, and not limitation, computer readable media may comprise "computer storage media" and "communications media."

"Computer storage media" include volatile and non-volatile, removable and non-removable media implemented in any method or technology for storage of information such as computer readable instructions, data structures, program modules, or other data. Computer storage media include, but are not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by a computer.

"Communication media" typically embody computer readable instructions, data structures, program modules, or other data in a modulated data signal, such as carrier wave or other transport mechanism. Communication media also include any information delivery media. The term "modulated data signal" means a signal that has one or more of its characteristics set or changed in such a manner as to encode information in the signal. By way of example, and not limitation, communication media include wired media such as a wired network or direct-wired connection, and wireless media such as acoustic, RF, infrared, and other wireless media. Combinations of any of the above are also included within the scope of computer readable media.

Generally, any of the functions or techniques described herein can be implemented using software, firmware, hardware (e.g., fixed logic circuitry), manual processing, or a combination of these implementations. The terms "module" and "component" as used herein generally represent software, firmware, hardware, or combinations thereof. In the case of a software implementation, the module, functionality, or logic represents program code that performs specified tasks when executed on a processor (e.g., CPU or CPUs). The program code can be stored in one or more computer storage media, further description of which may be found with reference to FIG. 6. The features of the concurrently displaying multiple trick streams for video techniques described herein are platform-independent, meaning that the techniques can be implemented on a variety of commercial computing platforms having a variety of processors.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. One or more computer storage media having stored thereon multiple instructions that, when executed by one or more processors, cause the one or more processors to:
   receive a request to display multiple different trick video streams corresponding to video content;
   concurrently display, in response to the request, multiple different windows, wherein at least one of the multiple windows is displayed over the video content;
   display, in each of the multiple different windows, a different one of the multiple different trick video streams for concurrent play back of the multiple different trick video streams, wherein at least one of the multiple different trick video streams is played back in a direction and at a speed that is different than the other different trick video streams and at least two of the multiple different trick video streams correspond to different versions of the same video content;
   receive a request to stop display of the multiple different trick video streams;
   receive a user selection of one of the multiple different windows; and
   play back the video content at a location corresponding to a current location of the trick video stream in the selected window.

2. One or more computer storage media as recited in claim 1, wherein the multiple different trick video streams comprise multiple fast-forward streams having different speeds.

3. One or more computer storage media as recited in claim 1, wherein the multiple different trick video streams comprise multiple rewind streams having different speeds.

4. One or more computer storage media as recited in claim 1, wherein the multiple different trick video streams comprise multiple slow-motion streams having different speeds.

5. One or more computer storage media as recited in claim 1, wherein the multiple different trick video streams comprise one or more fast-forward streams and one or more rewind streams.

6. One or more computer storage media as recited in claim 1, wherein each of the multiple different windows has a corresponding one of multiple identifiers, and wherein to receive the user selection is to receive user selection of a button, on a remote control device, corresponding to one of the multiple identifiers.

7. One or more computer storage media as recited in claim 1, wherein each of the multiple different windows comprises a picture-in-picture (PIP) window.

8. One or more computer storage media as recited in claim 1, wherein the multiple instructions further cause the one or more processors to generate, based on the video content, one or more of the multiple different trick video streams.

9. One or more computer storage media as recited in claim 1, wherein the multiple instructions further cause the one or more processors to close, in response to the user selection, the multiple different windows.

10. A computer-implemented method comprising:
    concurrently displaying, in multiple windows, multiple trick video streams corresponding to video content streams, the multiple trick video streams being concurrently played back in respective windows of the multiple windows, wherein at least one of the multiple windows is displayed over the video content, at least one of the multiple trick video streams is played back in a direction and at a speed that is different than the other trick video streams, and at least two of the multiple trick video streams correspond to different versions of the same video content;

receiving a user selection of one window of the multiple windows; and playing back the video content at a location corresponding to a location in a trick video stream being played back in the one window when the user selection is received.

11. A computer-implemented method as recited in claim 10, wherein the multiple trick video streams comprise multiple fast-forward streams having different speeds.

12. A computer-implemented method as recited in claim 10, wherein the multiple trick video streams comprise multiple rewind streams having different speeds.

13. A computer-implemented method as recited in claim 10, wherein the multiple trick video streams comprise multiple slow-motion streams having different speeds.

14. A computer-implemented method as recited in claim 10, wherein the multiple trick video streams comprise one or more fast-forward streams and one or more rewind streams.

15. A computer-implemented method as recited in claim 10, wherein each of the multiple windows comprises a picture-in-picture (PIP) window.

16. A device comprising:
a video content display module to receive and display video content;
a trick stream display module to concurrently display, in each of multiple windows, one of multiple trick video streams corresponding to the video content such that the multiple windows concurrently play back the multiple trick video streams, wherein at least one of the multiple windows is displayed over at least a portion of the video content that is displayed and the trick stream display module is configured to play back at least one of the trick video streams in a direction and at a speed that is different than at least one other of the trick video streams and to play back at least two of the multiple trick video streams that correspond to different versions of the same video content, the trick stream display module further configured to communicate to the video content display module a location of the video content corresponding to a user selection of one of the multiple different windows; and
wherein the video content display module is further to jump to displaying the video content at the location.

17. A device as recited in claim 16, wherein the multiple trick video streams comprise one or more fast-forward streams and one or more rewind streams.

18. A device as recited in claim 16, wherein each of the multiple windows comprises a picture-in-picture (PIP) window.

19. A device as recited in claim 16, wherein the trick stream display module is further configured to generate, based on the video content, one or more of the multiple trick video streams.

20. A device as recited in claim 16, wherein each of the multiple windows has a corresponding one of multiple identifiers, and wherein the user selection of one of the multiple different windows is a user selection of a button, on a remote control device, corresponding to one of the multiple identifiers.

* * * * *